US010332488B2

(12) United States Patent
Galu, Jr. et al.

(10) Patent No.: US 10,332,488 B2
(45) Date of Patent: Jun. 25, 2019

(54) GENERATING A SECURE STATE INDICATOR FOR A DEVICE USING A LIGHT PIPE FROM A FIXED POSITION ON THE DEVICE'S DISPLAY

(71) Applicant: Texas Instruments Incorporated, Dallas, TX (US)

(72) Inventors: James Joseph Galu, Jr., Richardson, TX (US); Thomas Brian Olson, Allen, TX (US); Michael Wayne Allen, Frisco, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 267 days.

(21) Appl. No.: 15/015,683

(22) Filed: Feb. 4, 2016

(65) Prior Publication Data

US 2016/0240051 A1 Aug. 18, 2016

Related U.S. Application Data

(60) Provisional application No. 62/116,690, filed on Feb. 16, 2015.

(51) Int. Cl.
*G08B 3/00* (2006.01)
*G09G 5/377* (2006.01)
*G09G 3/34* (2006.01)
*G09F 1/00* (2006.01)
*G06F 15/02* (2006.01)
*G16H 40/63* (2018.01)

(52) U.S. Cl.
CPC ............ *G09G 5/377* (2013.01); *G06F 15/02* (2013.01); *G09F 1/00* (2013.01); *G09G 3/34* (2013.01); *G16H 40/63* (2018.01)

(58) Field of Classification Search
None
See application file for complete search history.

(56) References Cited

U.S. PATENT DOCUMENTS

| 6,046,730 A * | 4/2000 | Bowen | H04M 1/022 |
| | | | 250/227.22 |
| 2009/0143141 A1* | 6/2009 | Wells | G07F 17/32 |
| | | | 463/37 |
| 2010/0069844 A1* | 3/2010 | Bonner | A61B 17/3478 |
| | | | 604/117 |
| 2012/0050646 A1* | 3/2012 | Huang | G09G 3/36 |
| | | | 349/65 |

OTHER PUBLICATIONS

"Ti-Nspire Press-to-Test Guidebook", Texas Instruments Incorporated, pp. 1-35, 2006-2015.
"Ti-83 series", Wikipedia, available at https://en.wikipedia.org/wiki/TI-83_series on Jan. 18, 2016, pp. 1-6.

* cited by examiner

*Primary Examiner* — Julie B Lieu
(74) *Attorney, Agent, or Firm* — Rose Alyssa Keagy; Charles A. Brill; Frank D. Cimino

(57) ABSTRACT

A handheld device is configured with a mode indicator to provide an easily seen indication of a defined mode of operation. A command may be received by the handheld device to enter the defined mode of operation. After entering the defined mode of operation, the device may set one or more specific pixels on a display of the handheld device to a predefined color indicative of the defined mode of operation. The mode indicator on the handheld is illuminated by transporting colored light generated by the one or more specific pixels to the mode indicator.

8 Claims, 4 Drawing Sheets

GENERATING A SECURE STATE INDICATOR FOR A DEVICE USING A LIGHT PIPE FROM A FIXED POSITION ON THE DEVICE'S DISPLAY

CLAIM OF PRIORITY UNDER 35 U.S.C. 119 (e)

The present application claims priority to and incorporates by reference U.S. Provisional Application No. 62/116,690, filed Feb. 16, 2015, entitled "Generating a Secure Unit State Indicator Using a Light Pipe From a Fixed Position on an LCD."

FIELD OF THE INVENTION

Embodiments of the present disclosure generally relate to assuring that a student's handheld device is in a proper condition for conducting an exam.

BACKGROUND OF THE INVENTION

Many school classrooms now encourage or require the use of handheld calculators in various math classes. During an examination, the mobile devices may be placed in an "exam mode" that may allow certain functionality of the handheld devices to be limited. For example, on TI-Nspire™ handhelds, a built-in Press-to-Test feature allows a user to easily comply with the rules for the use of calculators in exams by temporarily disabling all current documents and denying access to programming libraries. A blinking LED located at the top of an educational device handheld, such as the TI-Nspire™ or TI-83 Premium CE, may provide invigilators with a way to quickly and confidently see that a candidate's handheld is operating in Press-to-Test mode. After the exam, handhelds are easily restored for classroom use by exiting Press-to-Test mode and all previously created documents may be restored.

With ever increasing frequency, school classrooms are equipped with a classroom learning system in which digital devices, e.g., handheld calculators, for student use are connected to a host computer used by the teacher. Such a classroom learning system allows a teacher to perform actions such as creating and managing lessons, transferring files between the computer and the digital devices, monitoring student activity on the digital devices using screen captures, polling, assessments, etc., and performing various interactive activities with the students. Various tools are also provided for creating, distributing, and analyzing educational content. The TI-Nspire Navigator™ System from Texas Instruments Incorporated is an example of such a classroom learning system.

BRIEF DESCRIPTION OF THE DRAWINGS

Particular embodiments in accordance with the invention will now be described, by way of example only, and with reference to the accompanying drawings.

Figure 1:
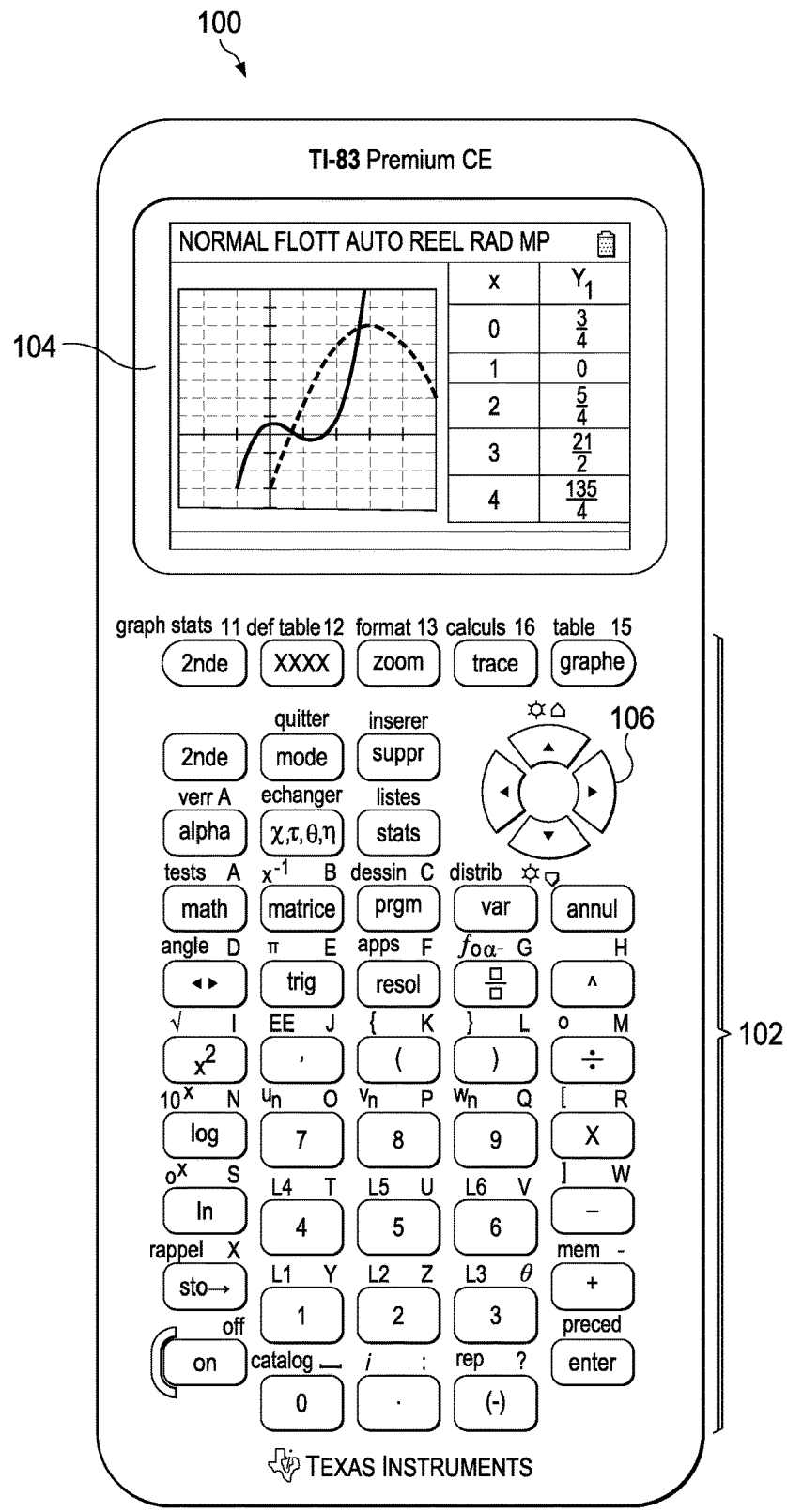
FIG. 1 is an illustration of an example handheld device.

Other features of the present embodiments will be apparent from the accompanying drawings and from the detailed description that follows.

DETAILED DESCRIPTION OF EMBODIMENTS OF THE INVENTION

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

It is desirable in a class room setting to provide an indication to a teacher that each student's handheld product is in a proper condition for conducting an exam. This may involve restricting functionality on the handheld product to permit only the functionality and information required by the exam and avoid any un-allowed functionality. In order to make it easier for a teacher or test proctor to determine if a student's handheld device is in the proper mode of operation for taking a test, prior handheld devices may have included an LED (light emitting diode) on a top edge of the handheld device's housing to provide an easily viewed mode indicator. A means of addressing the LED component may be provided for software running on the handheld device in order to provide a visual indication of the unit mode that is visible from a distance without checking the display of each student's handheld device.

In embodiments of the present disclosure, the light source for providing this indication is derived from using the handheld's display itself with the addition of a light pipe capturing light from a portion of the display and redirecting that light, including color information, to provide an indication of the state of the unit. In this manner, a lower cost mode indicator may be provided on a handheld device to indicate that it is in test mode.

FIG. 1 shows an example of a handheld device 100 in accordance with one or more embodiments of the disclosure. For illustrative purposes, the handheld device illustrated in FIG. 1 is similar to graphing calculators available from Texas Instruments Incorporated, such as a TI-83 Premium CE, for example. Handheld devices with more or fewer components may be used in other embodiments of the disclosure. As shown in FIG. 1, the handheld device 100 includes a display 104, and a keypad 102. In some embodiments a touchpad may be included in addition to or in place of arrow keys 106. The display 104 may be used to display, among other things, information input to applications executing on the handheld device 100 and various outputs of the applications. The display 104 may be, for example, an LCD (liquid crystal display) with a backlight. The keypad 102 allows a user, e.g., a student or instructor, to enter data and functions and to start and interact with applications executing on the handheld device 100. The keypad 102 may also include an alphabetic keyboard for entering text. Touch pad and/or arrow keys 106 allow a user to interact with the display 104 by translating the motion and position of the user's fingers on the touchpad and/or arrow keys 106 to provide functionality similar to using an external pointing device, e.g., a mouse. A user may use the touchpad and/or arrow keys 106 to perform operations similar to using a pointing device on a computer system, e.g., scrolling the display content, pointer positioning, selecting, highlighting, etc.

Figure 2:
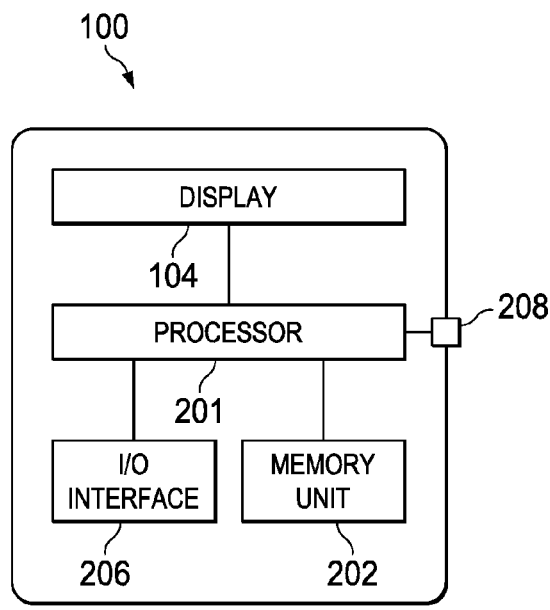
FIG. 2 is a block diagram of the handheld device of FIG. 1.

FIG. 2 is a block diagram of the handheld device 100 in accordance with one or more embodiments of the disclosure. The handheld device 100 includes a processor 201 coupled to a memory unit 202, which may include one or both of non-volatile memory for program storage, e.g., read-only memory (ROM), and memory for non-persistent data and program storage, e.g., random-access memory (RAM). In some embodiments, the non-volatile program storage memory stores software programs and the non-persistent memory stores intermediate data and operating results. An input/output port 208 may provide connectivity to external devices, e.g., a wireless adaptor or wireless cradle. In one or more embodiments, the input/output port 208 is a bi-directional connection such as a mini-AB USB port. Also included in the handheld device 100 are a display 104 and an I/O interface 206. The I/O interface 206 provides an interface to couple input devices such as the keypad 202 to the processor 201. In some embodiments, the handheld device 100 may also include an integrated wireless interface (not shown) or a port for connecting an external wireless interface (not shown). In some embodiments, memory unit 202 may store software instructions to be executed by the processor 201 to implement some or all of the device based operations for class activities and communication with a class room computer system.

The general operation and construction of handheld devices such as graphing calculators is well known and need not be described in further detail herein. See, for example, "TI-83 series", Wikipedia, updated 11 Dec. 2015, which is incorporated by reference herein.

Figure 3:
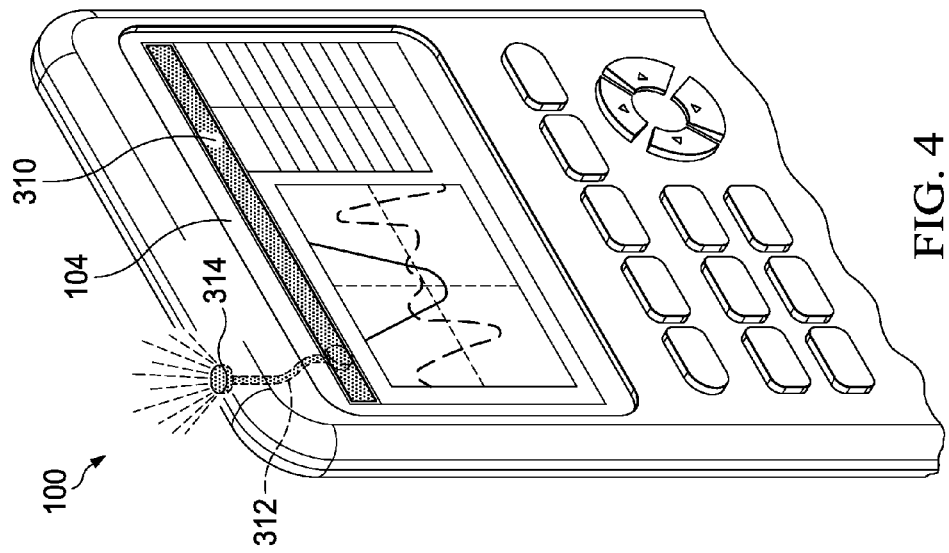
FIGS. 3-4 illustrate an example light pipe on the device of FIG. 1 for indicating a mode of operation.

FIG. 3 illustrates an example light pipe 312 that is included in handheld device 100 to provide an indication of a mode of operation. Light pipe 312 collects light that is produced by one or more specific pixels on display 104 and channels the light to the top of the handheld device where it may be emitted from an exposed end of the light pipe that forms mode indicator 314. While the general placement of light pipe 312 is illustrated in FIG. 3, typically in an actual device 100 only the tip of light pipe 312 would be visible to form mode indicator 314.

Figure 4:
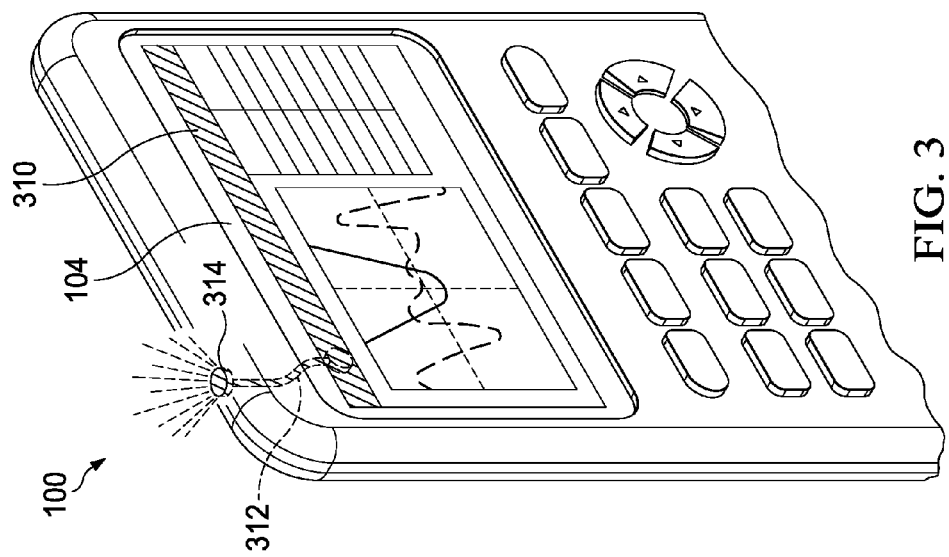

Light pipe 312 may simply be a clear piece of plastic with good optical properties that serves as an optical channel that steers light from one source to another location much like a periscope or a fiber optic cable does. The light pipe material may be built around display 104 and associated support plastics and routed to any other location on device 100. Specifically in the example application of a TI-83 Premium CE, the light pipe may wrap around the display 104 to a position on the upper left side of the display. By convention, the top region of the display indicated as region 310 is reserved for a status bar. The background color of the status bar region may be changed under control of software executed on device 100. For example, during a normal mode of operation, the status bar may be set by control software to be black, as illustrated in FIG. 3. While the device is in test mode, the status bar may be set by control software to be non-black, such as a color blue, as illustrated in FIG. 4.

Figure 5:
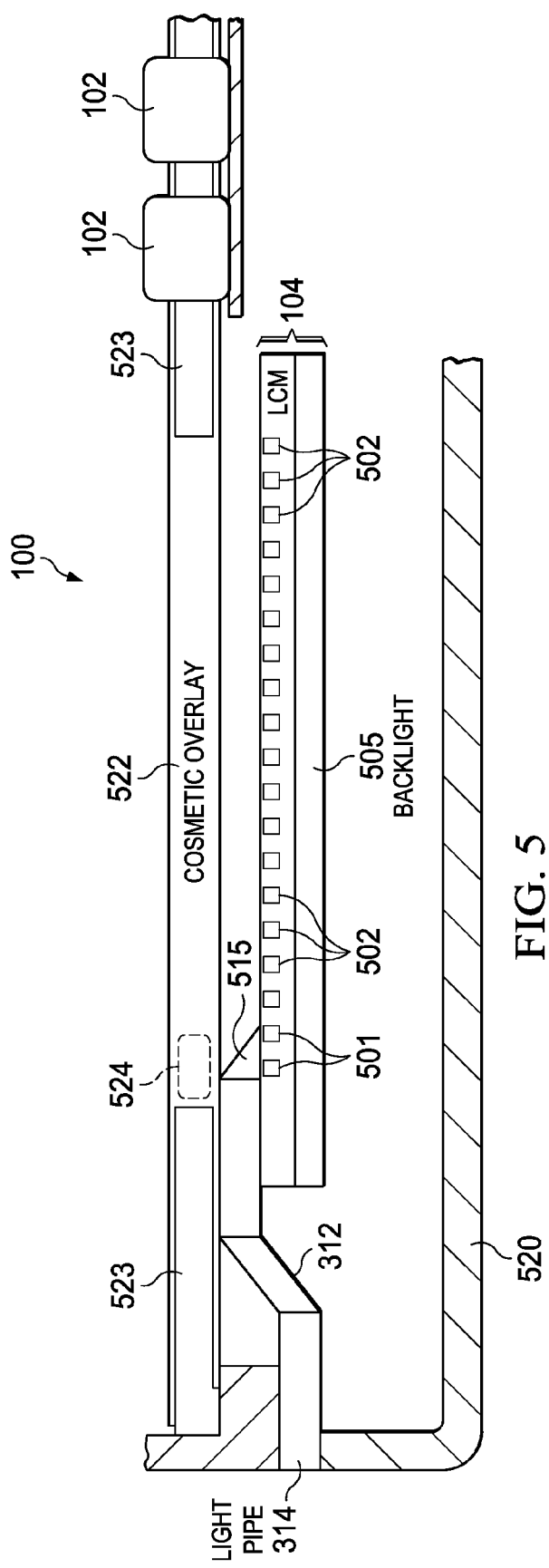
FIG. 5 is a cross sectional view of the device of FIG. 1 illustrating placement of the light pipe.

FIG. 5 is a cross sectional view of device 100 illustrating placement of the light pipe 312 in more detail. Handheld device 100 includes a housing 520 that surrounds the internal components. Display 104 is mounted within housing 520. Display 104 includes an array of pixels, generally indicated as 502. A cosmetic overlay 522 may be positioned in front of display 104 and keypad 102, referring again to FIG. 1. A portion of cosmetic overlay 522 may be clear so that an active region of display 104 that includes the array of pixels 502 is visible to a user, while the remainder of cosmetic overlay 522 may be opaque, as illustrated at 523. Cutouts may be provided for the keys of keypad 102.

The light Pipe's light collector (input side) 515 may be angled in such a way as to be nearly invisible to the user, yet still reflect enough light to be visible at the light pipe's output location that forms mode indicator 314. The light-pipe may only need to be positioned over a small area, such as a few specific pixels, as indicated at 501. The pipe may therefore be designed to overlap only a very small portion of the screen; for example, only 1-2 mm. Alternatively, a whole top row or a side row of the pixels may be used to collect the light output and thereby to increase brightness of the mode indicator.

In another embodiment, a portion of the display module's area may be obscured by the plastic housing so that it is not visible to the end user. For example, a portion of the cosmetic overlay that extends over the active region of display 104 may be opaque, such as the region indicated at 524. However, this obscured active region of display 104 may be used internally by the light pipe collector to pipe user readable signals to the top or side of the device.

In some embodiments, a software control program may designate a row of specific pixels either on the side or top of the screen for use by a light pipe. In this case, a plain sheet of plastic may be used to form a planar light pipe that is placed over that top or side row obscuring and redirecting the light from that row to the top or side of the unit.

In another embodiment, a reflective coating may be used on the light pipe to improve brightness.

In another embodiment, the light pipe may be implemented using a flexible fiber optic cable, for example.

Display 104 may include a backlight 505 that provides the light energy that is formed into an image under control of liquid crystals within display 104 that act as shutters to selectively allow passage of light. The operation of LCDs is well known and need not be described in detail herein. As described above in more detail, light energy provided by backlight 505 may be controlled by a one or more specific pixels in display 104 and then transferred to a mode indicator 314 by light pipe 312.

In another embodiment of this disclosure, a display may be formed by active pixels, rather than by a liquid crystal shutter mechanism. For example, active pixels may be formed by LEDs (light emitting diodes). In another embodiment, a flat panel plasma display may be used. In another embodiment, a deformable mirror device may be used as a display device, Embodiments of this disclosure are applicable to a wide range of known and later developed types of display that produce light that may be captured by a light pipe.

Figure 6:
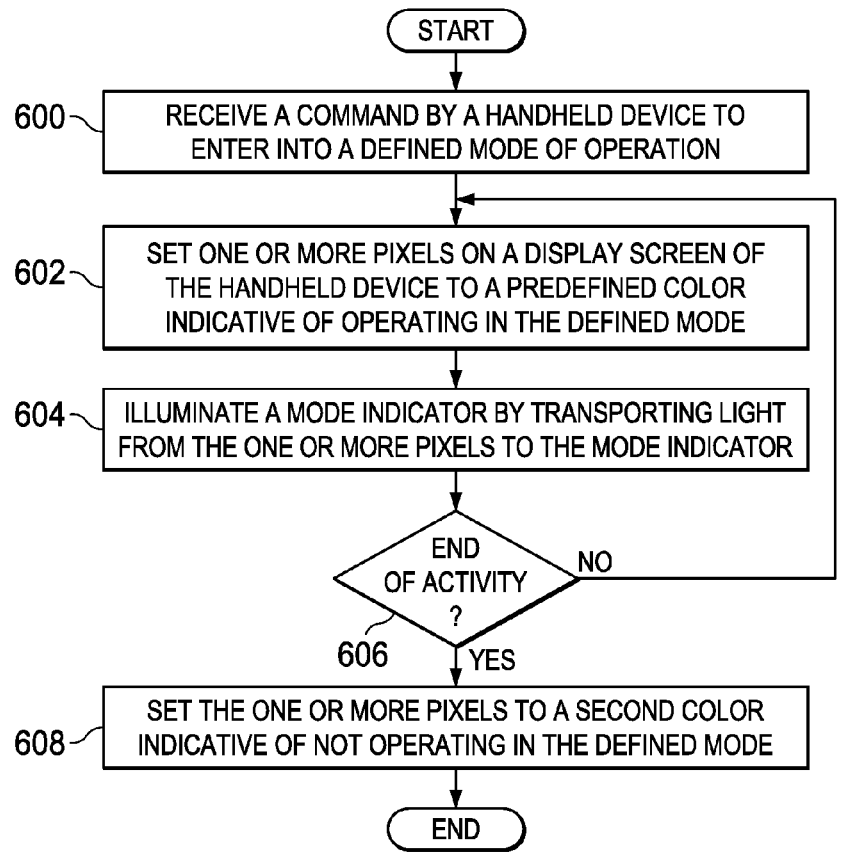
FIG. 6 is a flow diagram of a method for indicating a mode of operation of a handheld device.

FIG. 6 is a flow diagram of a method for indicating a mode of operation of a handheld device. The concept of placing the handheld in a limited functionality mode for use during an examination is well known. For example, see "TI-nspire Press-to-Test Guidebook", Texas Instruments, which is incorporated by reference herein. Press-to-Test temporarily disables documents and some features of handheld applications. After the exam, these documents and features may be easily restored for classroom use. A secure kernel of software controls the operation of the device.

When a user wants the handheld to be placed into test mode, the user may enter a specified key sequence. For example, to enter "press to test" mode, a user may hold down the "ESC" and the "ON" keys until a prompt menu is displayed on display 104. The user may then select from several options provided by the prompt menu, and then press the "enter" key to enter 600 the test mode.

As described with regard to FIGS. 3 and 4, when the handheld device enters test mode, control software may cause the header ribbon 310 to change 602 from black to blue, in this example. The software may be modified to change to any color and any blinking pattern desired in other embodiments.

As described in more detail above, the light produced by a few specific pixels in the header ribbon region may be captured by a light pipe and transported to an opposite end of the light pipe to illuminate 604 a mode indicator on a top or side of the handheld device that is easily visible to a teacher or test proctor, for example.

At the end of the test 606, the device may then receive a command from the user to return to a normal non-test mode of operation. Control software on device 100 may then set 608 the specific pixels to a second color, such as black in this example, which will then be transported to the mode indicator to indicate the device is now not operating in test mode.

The test mode indicator disclosed herein has several advantages over current devices. For example, current TI-83 Premium CE device uses an LED mounted on a printed circuit board (PCB) to drive a light pipe to indicate if the device is in test mode while the same device turns the Status Bar at the top of the device a fixed BLUE color.

A problem with the LED approach is that the LED can be compromised by software or hardware hacking. In an embodiment of the present disclosure, the light pipe can be caused to blink at a rate and color that matches a fixed position on the display. This presents a major challenge to a hardware hacker and would require a software hacker to change the well protected status bar on the device.

Another problem is that the LED costs more money than a light pipe. The current TI-83 uses both a light pipe and an LED. An embodiment of the present disclosure needs only a light pipe.

Another problem is that the LED on the current TI-83 consumes power and has a negative impact on the overall battery life. In an embodiment of the present disclosure, the lack of a LED component would allow for a longer battery life.

Thus, an embodiment of the present disclosure provides an easy to see test mode indicator that is less expensive, has better security, and allows a longer battery life than the current TI-83 device.

Other Embodiments

While the invention has been described with reference to illustrative embodiments, this description is not intended to be construed in a limiting sense. Various other embodiments of the invention will be apparent to persons skilled in the art upon reference to this description.

For example, embodiments are described in which the digital devices in the classroom are handheld calculators. Examples of other types of handheld computing devices include scientific calculators, advanced calculators able to upload and run software applications, handheld-sized limited-purpose computer devices, handheld-sized educational computer devices, handheld-sized portable computer devices, portable computer devices, personal digital assistants (PDA), palmtop computers, cellular or mobile telephones, and any combination thereof.

While a technique was described herein for entering test mode by holding a defined combination of keys on the device, other embodiments may use a different combination of keys, or a different sequence of operations.

Many classrooms provide a network onto which the handheld devices may be connected. In this case, a command may be provided by a teacher to cause all of the devices in the class room to enter into a test mode. A test mode indicator as described herein may provide a confirmation that each and every device has responded to the network command and entered into test mode.

While a test mode was described herein, in another embodiment a different mode of operation may be invoked and indicated by a light pipe mode indicator as described herein. For example, different levels of restriction may be indicated by different colors.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A method for operating a handheld device, the method comprising:
   receiving a command by the handheld device to enter a defined mode of operation;

performing an operation by the handheld device to enter the defined mode of operation;

setting one or more specific pixels of a plurality of pixels of a display of the handheld device to a predefined color indicative of the defined mode of operation; and illuminating a mode indicator on the handheld by transporting light generated by the one or more specific pixels to the mode indicator.

2. The method of claim 1, further including hiding the one or more specific pixels using a cosmetic overlay over a portion of the display.

3. The method of claim 1, in which light generated by the plurality of pixels is provided by a backlight.

4. The method of claim 1, in which the plurality of pixels are active pixels.

5. The method of claim 1, in which setting the one or more specific pixels is done in a manner that causes the mode indicator to blink.

6. A handheld device comprising:

a housing;

a display mounted on the housing, the display having an array of individually illuminable pixels;

processing logic controllably coupled to the display, the processing logic being coupled to storage circuitry that stores instruction code executable by the processing logic; and a light pipe with a first end configured to receive illumination from one or more specific pixels of the array of individually illuminable pixels and a second end positioned at an opening in the housing to form a mode indicator.

7. The handheld device of claim 6, further including an opaque overlay positioned over the one or more specific pixels.

8. The handheld device of claim 6, further including a backlight positioned behind the array of individually illuminable pixels.

* * * * *